(12) United States Patent
Michailovski et al.

(10) Patent No.: US 12,275,019 B2
(45) Date of Patent: Apr. 15, 2025

(54) METHOD FOR FLOTATION OF A SILICATE-CONTAINING IRON ORE WITH A CATIONIC COLLECTOR

(71) Applicant: BASF SE, Ludwigshafen am Rein (DE)

(72) Inventors: Alexej Michailovski, Ludwigshafen (DE); Alexander Panchenko, Ludwigshafen (DE); Hannes Ferdinand Zipfel, Ludwigshafen (DE); Martin Ernst, Ludwigshafen (DE); Gabriela Budemberg, Ludwigshafen (DE); Stefanov Nedko Drebov, Ludwigshafen (DE); Sylvia von Krog, Ludwigshafen (DE); Tamara Kuelzer, Ludwigshafen (DE); Long Phan, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 624 days.

(21) Appl. No.: 17/606,997

(22) PCT Filed: Apr. 27, 2020

(86) PCT No.: PCT/EP2020/061604
§ 371 (c)(1),
(2) Date: Oct. 27, 2021

(87) PCT Pub. No.: WO2020/221685
PCT Pub. Date: Nov. 5, 2020

(65) Prior Publication Data
US 2022/0212204 A1 Jul. 7, 2022

(30) Foreign Application Priority Data
Apr. 30, 2019 (EP) ..................................... 19171801

(51) Int. Cl.
*B03D 1/01* (2006.01)
*C07C 215/18* (2006.01)

(52) U.S. Cl.
CPC .............. *B03D 1/01* (2013.01); *C07C 215/18* (2013.01); *B03D 2201/02* (2013.01); *B03D 2203/04* (2013.01)

(58) Field of Classification Search
None
See application file for complete search history.

(56) References Cited

U.S. PATENT DOCUMENTS

| 4,168,227 A | 9/1979 | Polgaire et al. |
| 4,760,189 A * | 7/1988 | Mercier ................ C07C 213/02 564/483 |
| 2009/0194466 A1* | 8/2009 | Hines ..................... B03D 1/008 209/166 |

FOREIGN PATENT DOCUMENTS

| CA | 1273024 A | 8/1990 |
| CA | 2205885 A1 | 12/1997 |

(Continued)

OTHER PUBLICATIONS

Rao and Leja,"Surface Chemistry of Froth Flotation", vol. 1: Fundamentals, Second Edition, 2004, excerpts from Section 1.7-1.9 (Year: 2004).*

(Continued)

*Primary Examiner* — Magali P Slawski
*Assistant Examiner* — Marriah C G Ellington
(74) *Attorney, Agent, or Firm* — Faegre Drinker Biddle & Reath LLP

(57) ABSTRACT

The invention relates to a method for manufacturing a concentrate enriched in iron mineral content from an ore, which contains an iron mineral and silicate, by reverse flotation, which method comprises the step of (c) adding a compound of formula I wherein $R^1$ is $C_9$-$C_{22}$ alkyl or alkenyl, which is linear or branched, $R^2$ is H, $C_1$-$C_4$ alkyl, which is linear or branched, $R^3$ is —X—$NH_2$, H or $C_1$-$C_4$ alkyl, which is linear or branched, and X is $C_2$-$C_4$ alkylene, which is linear or branched, or a salt of a protonated compound of formula I and an anion, to a prepared aqueous pulp of the ore and optionally one or more flotation auxil- (Continued)

iaries to obtain an aqueous mixture. Furthermore, a method for manufacturing a specific group of compounds of formula I, i.e. compounds of formula 1-X wherein $R^1$ is $C_9$-$C_{15}$ alkyl, which is linear or branched, $R^2$ is H, $R^3$ is —X—$NH_2$ and X is $C_2$-$C_4$ alkylene, which is linear or branched, is disclosed.

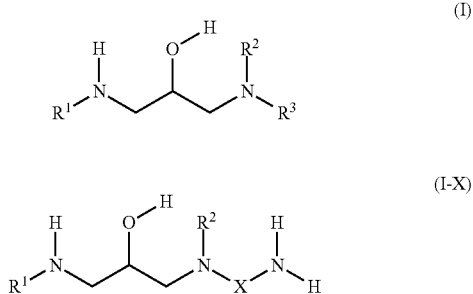

11 Claims, 8 Drawing Sheets

(56) References Cited

FOREIGN PATENT DOCUMENTS

| CA | 2205886 A1 | 12/1997 | |
| CA | 2831166 A1 * | 10/2012 | ............... B03D 1/01 |
| GB | 957723 A | 5/1964 | |
| GB | 1343957 A | 1/1974 | |
| GB | 2148294 A | 5/1985 | |
| SE | 421177 B | 12/1981 | |
| WO | WO-2008/077849 A1 | 7/2008 | |
| WO | WO-2012/139985 A2 | 10/2012 | |

OTHER PUBLICATIONS

European Search Report for EP Patent Application No. 19171801.4, Issued on Jan. 7, 2020, 3 pages.

International Search Report for PCT Patent Application No. PCT/EP2020/061604, Issued on Aug. 13, 2020, 3 pages.

* cited by examiner

METHOD FOR FLOTATION OF A SILICATE-CONTAINING IRON ORE WITH A CATIONIC COLLECTOR

The present invention relates to a method for manufacturing a concentrate enriched in iron mineral content from an ore, which contains an iron mineral and silicate, by a reverse flotation using 3-amino-2-hydroxypropylamine derivatives. Further embodiments are a use of the 3-amino-2-hydroxypropylamine derivatives as a flotation collector, specific 3-amino-2-hydroxypropylamine derivatives as such and a method for manufacturing the specific 3-amino-2-hydroxypropylamine derivatives.

A typical iron ore beneficiation process requires a flotation stage to remove silica ($SiO_2$) from the valuable iron mineral, e.g. oxides like hematite or magnetite, and thus to obtain a high-grade iron mineral concentrate. A high-grade iron mineral concentrate allows to make high quality steel. Removal of $SiO_2$ from different ores by froth flotation in combination with hydrophobic amines is a well-known process. Negatively charged silicate particles can be hydrophobized using suitable amines. Injection of air in a flotation cell leads to formation of hydrophobic gas bubbles, which can transport the hydrophobized silicate particles to the top of the flotation cell. The formed froth, which can be stabilized by a suitable chemical acting as a froth regulator, contains the hydrophobized silicate particles. Finally, the froth will be removed from the top and the enriched mineral is left at the bottom of the flotation cell.

CA 1273024 discloses a process and compositions for the froth flotation beneficiation of iron minerals from iron ores containing silicate and phosphate minerals, comprising as collectors a combination of a primary amine and a nitrogen compound containing an anionic group selected from methylene carboxylic acid, ethylene phosphoric acid and methylene phosphonic acid. The primary amine has the general formula $R_1$—[$OC_{n1}H_{2n1}$]$_{m1}$—[$NHC_{n2}H_{2n2}$]$_{m2}$—$NH_2$, wherein $R_1$ is a hydrocarbon group having from six to eighteen carbon atoms, n1 and n2 are 2 or 3; and m1 is from 0 to 1 and m2 is from 0 to 1. In a control example and examples 3 to 13, ($C_{8-10}H_{17-21}$)—O($CH_2$)$_3$—$NH_2$ is employed. In example 1, $C_{10}H_{21}$—$NH_2$ is employed. In example 2, $C_{10}H_{21}$O($CH_2$)$_3$—NH—($CH_2$)$_3$$NH_2$ is employed.

CA 2205885 discloses alkyl amines, alkyl diamines, alkyl polyamines, ether amines, and ether polyamines, neutralized with C3-24 carboxylic acids, which have improved fluidity and in some cases form stable dispersions in water. They are effective in froth flotation of impurities from ore. In particular, the removal of siliceous impurities from iron ore at high pH is mentioned. Preferred alkyl diamines have the formula ($R^6$)($R^7$)N($CH_2$)$_{2-3}$N($R^8$)($R^9$), wherein each of $R^6$, $R^7$, $R^8$ and $R^9$ is alkyl containing 1 to 30 carbon atoms or $R^7$, $R^8$ and/or $R^9$ can be hydrogen. The groups $R^{6-9}$ can be linear, branched, cyclic or aromatic. Alkyl polyamines include those having the formula X-(alk-N($R^{10}$))$_p$—Y, wherein X is —$NH_2$ or —H, p is 2 to 10, each alk group is independently alkylene containing 1 to 6 carbon atoms, each $R^{10}$ is independently —H or alkyl containing 1 to 22 carbon atoms, and Y is —H, alkyl containing 1 to 22 carbon atoms, or alkenyl containing 2 to 22 carbon atoms. In the examples, coco fatty primary amine, n-dodecyl ether primary amine, isododecyl ether amine and an ether amine corresponding to the formula ($C_8$-$C_{10}$ alkyl)-O—$CH_2$—$CH_2$—$CH_2$—$NH_2$ are employed.

CA 2205886 discloses alkyl amines, alkyl diamines, alkyl polyamines, ether amines, and ether polyamines, neutralized with C3-24 carboxylic acids, which offer improved liquidity and stability, and readily form stable, monophasic dispersions in water. They are effective in froth flotation of siliceous impurities from ores such as magnetic and hematite iron ores at high pH. Preferred alkyl diamines have the formula ($R^6$)($R^7$)N($CH_2$)$_{2-3}$N($R^8$)($R^9$), wherein each of $R^6$, $R^7$, $R^8$ and $R^9$ is alkyl containing 1 to 30 carbon atoms or $R^7$, $R^8$ and/or $R^9$ can be hydrogen. The groups $R^{6-9}$ can be linear, branched, cyclic or aromatic. Alkyl polyamines include those having the formula X-(alk-N($R^{10}$))$_p$—Y, wherein X is —$NH_2$ or —H, p is 2 to 10, each alk group is independently alkylene containing 1 to 6 carbon atoms, each $R^{10}$ is independently —H or alkyl containing 1 to 22 carbon atoms, and Y is —H, alkyl containing 1 to 22 carbon atoms, or alkenyl containing 2 to 22 carbon atoms. In the examples, coco fatty primary amine, n-dodecyl ether primary amine, isododecyl ether amine, an ether amine predominantly corresponding to the formula $R^3$—O—$R^4$—NH—$R^5$—$NH_2$ with $R^3$ being linear $C_{14}$ alkyl and $R^4$ and $R^5$ being linear $C_3$ alkyl, and an ether diamine predominantly corresponding to the formula $R^3$—O—$R^4$—NH—$R^5$—$NH_2$ with $R^3$ being a mixture of linear $C_{12}$ and $C_{14}$ alkyl and $R^4$ and $R^5$ being linear $C_3$ alkyl are employed.

SE 421177 discloses that oxide minerals such as mineral iron and mineral calcium are enriched by separating the siliceous species by foam floatation. As the collecting reagent in the process, a combination of ether diamine and fatty amine is used. The procedure achieves a decrease in the degree of contamination without lowering the requirements for good yield. A means for carrying out the method contains a combination of an ether diamine and a fatty amine, preferably a fatty diamine, where the ether diamine is present in excess weight and the ratio between the ether diamine and the fatty amine is greater than 1.0:1. In the examples, N-(3-dodecoxylpropyl)-propylene diamine, dodecyl-1,3-propylene diamine, 3-dodecoxypropylene amine, N-(3-nonoxy-propyl)propylene diamine, N-(3-decoxypropyl)propylene diamine, N-(3-undecoxypropyl) propylene diamine, coco-1,3-propylene diamine and coco amine are employed.

U.S. Pat. No. 4,168,227 discloses a method for enriching oxidized ores by froth flotation. Use is made, as collector, of a combination comprising: at least a first compound selected among amino-1-alkane products having the general formula $R_1$—(NH—$CH_2$—$CH_2$—$CH_2$)$_n$—$NH_2$, wherein $R_1$ is a saturated or unsaturated straight- or branched-chain hydrocarbon group containing from 8 to 18 carbon atoms, and n is an integer ranging from 0 to 3, and at least a second compound selected among amino-ether products having one amino function and at least one ether function, of the general formula $R_2$—O—($CH_2$—$CH_2$—O)$_n$—$CH_2$—$CH_2$—$CH_2$—$NH_2$, wherein $R_2$ is a saturated or unsaturated straight- or branched-chain hydrocarbon group containing from 2 to 18 carbon atoms, and n is an integer ranging from 0 to 2. In the examples, the alkylamine is a fatty amine extracted from copra, a first etheramine is R—O—$CH_2$—$CH_2$—$CH_2$—$NH_2$ with R resulting from a mixture of n-octanol and n-decanol, a second etheramine is R—O—$CH_2$—$CH_2$—$CH_2$—$NH_2$ with R resulting from n-decyclic alcohol, a third etheramine is R—O—$CH_2$—$CH_2$—$CH_2$—$NH_2$ with R resulting from mono-hexyclic ether of ethylene glycol, and a forth etheramine is R—O—$CH_2$—$CH_2$—$CH_2$—$NH_2$ with R resulting from n-octanol.

GB 1343957 discloses that niobium oxide ores, e.g. pyrochlore, microlite or perowskite, containing slimes are enriched by converting the ground ore to an aqueous pulp, and subjecting the pulp to froth flotation after the addition of a froth generating substance and a flotation collector for fixing the ore particles rich in niobium to the froth. The flotation collector is consisting of at least one aliphatic polyamine having the general formula R—[NH—(CH$_2$)$_p$]$_n$—NH$_2$, where n is greater than 1, p is from 2 to 6 and R is a hydrocarbon radical having from 8 to 22 carbon atoms, preferably 16 to 18 carbon atoms. A gangue depressing agent may be added to the pulp. Polyamines specified as collectors are N-alkyl-dipropylenetriamine and N-alkyl-tripropylene-tetramine and mixtures thereof. To facilitate their dispersion or solution in water, the polyamines may be at least partially treated with hydrochloric acid to form an amine salt or with a solvent. In the examples, N-alkyl-dipropylene triamine and N-alkyl tripropylene tetramine and a diamine are employed. The employed alkyl moiety is not further specified.

GB 957723 discloses that solid particles are surface treated with an aqueous emulsion of a compound R—[NH—(CH$_2$)$_p$]$_n$—NH$_2$ wherein R is a C8-C22 saturated, unsaturated, straight or branched chain, aliphatic or cycloaliphatic hydrocarbon group (or the corresponding acyl group); n is an integer from 2 to 5 and p is 2 or 3. The compounds can be mixed with kerosene, spindle oil, anthracene oil, soya bean oil or tallow fat. Specified polyamines for preparing the compounds are dipropylene triamine, tripropylene tetramine and tetrapropylene pentamine. In the examples, a dipropylene triamine, a tripropylene tetramine and a tetrapropylene pentamine are said to having been prepared from tallow fatty acid of which the carbon chains contain essentially from 16 to 18 carbon atoms, one part of the chain, which contain 18 carbon atoms, having a double bound. These 3 polyamines are employed in the examples.

WO 2008/077849 discloses a reverse froth flotation process for removal of silicates from iron ore having K$_{80}$≥110 micrometres using formulations comprising alkyl ether diamine and alkyl ether monoamine, alkylamine or alkyl diamine. The collecting composition comprises a first component a) which can be described by the general formula (I) R$^1$O-A-NH(CH$_2$)$_n$NH$_2$, wherein R$^1$ is a straight or branched hydrocarbyl group with 12-15 carbon atoms, A is a group CH$_2$CHXCH$_2$—, wherein X is hydrogen or a hydroxyl group, and n is a number 2-6; and a second component b) which is suitably selected from the group of compounds described by the formulae R$^2$NH$_2$ (IIa), R$^3$NHC$_3$H$_6$NH$_2$ (IIIa), R$^2$OC$_3$H$_6$NH$_2$ (IIb), and R$^3$OC$_3$H$_6$NHC$_3$H$_6$NH$_2$ (IIIb), wherein R$^2$ is a straight or branched hydrocarbyl group with 12-24 carbon atoms and R$^3$ is a straight or branched hydrocarbyl group with 16-24 carbon atoms. In the examples, N-(3-isotridecoxypropyl)-1,3-propane diamine, N—(C8-C10 alkoxypropyl)amine, N—(C12 alkoxypropyl) amine, N—(C14-C15 alkoxypropyl)amine, oleylamine, (coco alkyl)amine, N-(tallow alkyl)-1,3-propane diamine, N-(oleyl)-1,3-propane diamine, N—(C12 alkoxypropyl)-1,3-propane diamine, N-(coco alkyl)-1,3-propane diamine, N-(isotridecoxypropyl)amine, (C10-alkyl)amine and N—(C12 alkoxypropyl)-1,3-propane diamine are employed.

WO 2012/139985 discloses compounds of the formulae: RO—X—NH$_2$ (Ia); RO—X—NH$_3$$^+$Y$^-$ (Ib); RO—X—NH—Z—NH$_2$ (IIa); and RO—X—NH—Z—NH$_3$$^+$Y$^-$ (IIb), in which X is an aliphatic alkylene group containing 2 to 6 carbon atoms; Z is an aliphatic alkylene group containing 2 to 6 carbon atoms; Y— is an anion; and R is an aliphatic iso-C$_{13}$H$_{27}$— group with average branching degree ranging from 1.5 to 3.5. The compounds are particularly suitable as flotation collectors for enriching an iron mineral from a silicate-containing iron ore. In the examples, iso-C$_{13}$H$_{27}$—CH$_2$—CH$_2$—CH$_2$—NH$_2$ with an average branching degree of 2.0 to 2.4, iso-C$_{13}$H$_{27}$—O—CH$_2$—CH$_2$—CH$_2$—NH— CH$_2$—CH$_2$—CH$_2$—NH$_2$ with an average branching degree of 2.0 to 2.4, iC12oxypropylamine, iC13oxypropyl-1,3-propane diamine, iC12oxypropyl-1,3-propane diamine and 3,6,8,8-tetramethylnonane-1-amine are employed.

U.S. Pat. No. 4,760,189 discloses a process for the preparation of compounds of the formula R—NH—CH$_2$—CH(OH)—CH$_2$—NH$_2$, in which R is C$_1$ to C$_{30}$ alkyl radical, characterized in that ammonia is reacted with the compound of formula R—NH—CH$_2$—CH(OH)—CH$_2$—X, in which R has the given meaning and X is a halogen atom. The bactericidal activity of some of the compounds is tested.

GB 2148294 discloses salts having the formula Y—NH$_3$$^+$ RCO$_2$— (I) in which Y is a group of formula R$^1$XCH$_2$CH(OH)CH$_2$—, R and R$^1$ are the same or different and each is a straight- or branched alkyl group having from 1 to 18 carbon atoms, a straight- or branched chain alkenyl group having from 2 to 18 carbon atoms, a cycloalkyl group having from 4 to 12 ring atoms, an aryl group having 6-10 ring atoms, or an aralkyl group having from 7 to 10 carbon atoms; and X is O, CO$_2$, NH, NR$^2$ or S(R$^2$ is a straight- or branched chain alkyl group having from 1 to 18 carbon atoms or an alkenyl group having from 2 to 18 C atoms). These salts are useful as corrosion inhibitors.

There is still a need for improved methods in inverse flotation of ores containing iron mineral and silicate. Especially the quality of ores has been decreasing. With higher SiO$_2$ content in the ore, a selective removal of silicate is more difficult than in the past with ores of a lower SiO$_2$ content. On one side, a loss of iron mineral in the flotation process should be avoided, i.e. a high recovery, and on the other side, SiO$_2$ content should be decreased in a concentrate enriched in iron mineral content to a low level, i.e. selectivity. Especially for direct reduction processes using the concentrate, a low SiO$_2$ content is desirable. Typically, a mine as an ore processing site will set a maximum level of residual SiO$_2$ content that is allowed to remain in the concentrate at the end of the flotation process. This may for instance be 2% by weight. The target is generally to at least achieve this maximum silica level without significantly losing any of the iron mineral content. A better recovery in combination with a comparable or a better selectivity reduces iron mineral losses in the tailings and leads to economic benefits.

It is an object of the present invention to provide a method for manufacturing a concentrate enriched in iron mineral content with a high recovery of iron mineral from the applied ore and a low content of SiO$_2$ from the applied ore. At the same time, it is an advantage if a material applied in the method can economically be manufactured in a chemically relatively pure and thus homogenous form. A chemically relatively pure material offers via combination with other materials, particularly other co-collectors, a fine-tuned adjustment to a specific ore.

The object is achieved, according to the invention, by a method for manufacturing a concentrate enriched in iron mineral content from an ore, which contains an iron mineral and silicate, by a reverse flotation, which method comprises the step of (c) adding a compound of formula I

(I)

wherein $R^1$ is $C_9$-$C_{22}$ alkyl or alkenyl, which is linear or branched, $R^2$ is H, $C_1$-$C_4$ alkyl, which is linear or branched, $R^3$ is —X—$NH_2$, H or $C_1$-$C_4$ alkyl, which is linear or branched, and X is $C_2$-$C_4$ alkylene, which is linear or branched, or a salt of a protonated compound of formula I and an anion, to a prepared aqueous pulp of the ore and optionally one or more flotation auxiliaries to obtain an aqueous mixture.

Preferably, the method for manufacturing a concentrate enriched in iron mineral content from an ore, which contains an iron mineral and silicate, by a reverse flotation, comprises the step of (c) adding an amine to a prepared aqueous pulp of the ore and optionally one or more flotation auxiliaries to obtain an aqueous mixture, characterized in that the amine is a compound of formula I (I)

wherein $R^1$ is $C_9$-$C_{22}$ alkyl or alkenyl, which is linear or branched, $R^2$ is H, $C_1$-$C_4$ alkyl, which is linear or branched, $R^3$ is —X—$NH_2$, H or $C_1$-$C_4$ alkyl, which is linear or branched, and X is $C_2$-$C_4$ alkylene, which is linear or branched, or a salt of a protonated compound of formula I and an anion.

Preferably, the method for manufacturing a concentrate enriched in iron mineral content from an ore, which contains an iron mineral and silicate, comprises the steps of (a) providing the ore, which contains an iron mineral and silicate, (b) preparing from the provided ore by addition of water and optionally one or more flotation auxiliaries an aqueous pulp, (c) adding a compound of formula I (I)

wherein $R^1$ is $C_9$-$C_{22}$ alkyl or alkenyl, which is linear or branched, $R^2$ is H, $C_1$-$C_4$ alkyl, which is linear or branched, $R^3$ is —X—$NH_2$, H or $C_1$-$C_4$ alkyl, which is linear or branched, and X is $C_2$-$C_4$ alkylene, which is linear or branched, or a salt of a protonated compound of formula I and an anion, to the prepared aqueous pulp of the ore and optionally one or more flotation auxiliaries to obtain an aqueous mixture, (d) aerating the aqueous mixture in a flotation cell to generate a froth, which is enriched in silicate content, and removing the generated froth from the flotation cell, (e) obtaining from the flotation cell the concentrate enriched in iron mineral content.

The steps (a), (b), (c), (d) and (e) describe more detailed the reverse flotation.

The ore, which contains an iron mineral and silicate ($SiO_2$), is for example from a magmatic deposit or from a sedimentary deposit. The step (a) of providing an ore comprises for example also a crushing or a grinding respectively milling of the ore. In case of an ore from a magmatic deposit, the step of providing the ore comprises for example also a crushing of the ore and a grinding respectively milling of the ore. In case of an ore from a sedimentary deposit, the step of providing the ore comprises for example a crushing of the ore, particularly a crushing of the ore and a wet grinding of the ore. Preferably, the step (a) of providing of the ore results in ore particles, which have a particle size allowing 60% to 100% by weight of the particles based on the overall weight of the particles to pass a 100 μm steel mesh sieve as measured by standard dry sieving.

The ore contains for example 20% to 80% by weight of silicate based on the weight of the ore, particularly 25% to 75% by weight, very particularly 30% to 55% by weight and especially 30% to 40% by weight.

Preferably, the iron mineral consists out of 90% to 100% by weight of iron oxide based on all iron mineral in the ore. Very preferably, the iron mineral consists out of at least 97% to 100% by weight of iron oxide, particularly preferably out of 99% to 100%. Typical iron oxides are hematite ($Fe_2O_3$ with 69.9% by weight of iron content), magnetite ($Fe_3O_4$ with 72.4% by weight of iron content) or a mixture of both. The weight of iron content is similar to a weight content of Fe atoms.

A typical ore comprises between 40% to 70% by weight of hematite and 30% to 50% by weight of silica, particularly 45% to 65% by weight of hematite and 30% to 45% by weight of silica. Preferred is an ore, which comprises iron mineral, wherein more than 50% by weight of the comprised iron mineral is an iron oxide, which is hematite. Very preferred, more than 70% to 100% is an iron oxide, which is hematite.

The compound of formula I acts in the method as a collector for froth flotation.

The compound of formula I carries an asymmetric carbon atom, i.e. the carbon atom substituted with the hydroxy group. This leads to two enantiomers. In case of a branched substituent $R^1$, an additional asymmetric carbon atom is possible depending on the position of the branching at the substituent. This leads to diastereomers.

$C_9$-$C_{22}$ alkyl or alkenyl, which is linear or branched, is for example n-nonyl, 2-methyloctyl, 7-methyloctyl, n-decyl, 2-methylnonyl, 8-methylnonyl, n-undecyl, 2-methyldecyl, 9-methyldecyl, n-dodecyl, 2-methylundecyl, 10-methylundecyl, n-tridecyl, 2-methyldodecyl, 11-methyldodecyl, 2,10-dimethylundecyl, 7,10-dimethylundecyl, 2,6,9-trimethyldecyl, 2,7,9-trimethyldecyl, 3,6,9-trimethyldecyl, 2,4,6,8-tetramethylnonyl, n-tetradecyl, 2-methyltridecyl, 12-methyltridecyl, n-pentadecyl, 2-methyltetradecyl, 13-methyltetradecyl, n-hexadecyl, 2-methylpentadecyl, 14-methylpentadecyl, n-heptadecyl, 2-methylhexadecyl, 15-methylhexadecyl, n-octadecyl, 2-methylheptadecyl, 16-methylheptadecyl, (E)-octadec-9-enyl, (Z)-octadec-9-enyl, (E)-octadec-11-enyl, (Z)-octadec-11-enyl, (9Z,12Z)-octadeca-9,12-dienyl, n-nonadecyl, 2-methyloctadecyl, 17-methyloctadecyl, n-icosyl, 2-methylnonadecyl, 18-methylnonadecyl, n-henicosyl, 2-methylicosyl, 19-methylicosyl, n-docosyl, 2-methylhenicosyl or 20-methylhenicosyl. Preferred is $C_9$-$C_{18}$ alkyl, which is linear or branched, or $C_{18}$-alkenyl, which is linear. Very preferred is $C_9$-$C_{15}$ alkyl, which is linear or branched. Particularly preferred is $C_{10}$-$C_{14}$ alkyl, which is linear or branched. Very particularly preferred is $C_{12}$-$C_{14}$ alkyl, which is linear or branched. Especially preferred is $C_{12}$-$C_{14}$ alkyl, which is linear. Very especially preferred is $C_{12}$ alkyl, which is linear (=n-dodecyl).

$C_1$-$C_4$ alkyl, which is linear or branched, is for example methyl, ethyl, n-propyl, 2-methylethyl, n-butyl, 1-methylpropyl, 2-methylpropyl or 1,1-dimethylethyl. Preferred is $C_1$-$C_4$ alkyl, which is linear. Very preferred is methyl or ethyl, particularly preferred is methyl.

$C_2$-$C_4$ alkylene, which is linear or branched, is for example —$CH_2$—$CH_2$—, —$CH_2$—$CH_2$—$CH_2$—, —$CH_2$—$C(CH_3)H$— (=1-methylethylene), —$CH_2$—$CH_2$—$CH_2$—$CH_2$—, —$CH_2$—$C(CH_3)H$—$CH_2$—$CH_2$— or —$C(CH_3)H$—$C(CH_3)H$—. Preferred is $C_2$-$C_3$ alkylene, which is linear or branched. Very preferred is —$CH_2$—$CH_2$— or —$CH_2$—$CH_2$—$CH_2$—.

In case $R^3$ is —X—$NH_2$, formula I is also expressed as formula I-X

(I-X)

The anion is the deprotonated form of an acid A(-H)p, wherein —H represents an acidic proton and p the number of acidic protons of the acid A(-H)p. Depending on the acid strength of the acid A(-H)p, some acidic protons of the acid A(-H)p might not be deprotonated in a salt with a compound of formula I.

A salt of a protonated compound of formula I and the anion is also expressed in case of $R^3$ is H or $C_1$-$C_4$ alkyl, which is linear or branched, by formulae I-t1-1+, I-t2-1+ or I-t1-2+ and in case of $R^3$ is —X—$NH_2$ by formulae I-X-t1-1+, I-X-t2-1+, I-X-t3-1+, I-X-t1-2+, I-X-t2-2+, I-X-t3-2+ or I-X-t1-3+

(I-t1-1+)

(I-t2-1+)

(I-t1-2+)

(I-X-t1-1+)

(I-X-t2-1+)

(I-X-t3-1+)

(I-X-t1-2+)

(I-X-t2-2+)

(I-X-t3-2+)

(I-X-t1-3+)

wherein A represents the anion, y is an integer, which is at least 1, and y represents the negative charge of the anion. y is not higher than p, which is the number of acidic protons of the acid A(-H)p. Preferred is an anion, which is a deprotonated acid A(-H)p, wherein p is 1, 2 or 3 and y is 1 for p=1, y is 1 or 2 for p=2 and y is 1, 2, or 3 for p=3.

Formulae I-t1-1+ and I-t2-1+ describe tautomeric forms of the same salt. Formulae I-X-t1-1+, I-X-t2-1+ and I-X-t3-1+ describe tautomeric forms of the same salt. Formulae I-X-t1-2+, I-X-t2-2+ and I-X-t3-2+ describe tautomeric forms of the same salt.

The anion is for example $C_1$-$C_{18}$ carboxylate, fluoride, chloride, bromide, iodide, sulfonate, hydrogensulfate, sulfate, dihydrogenphosphate, hydrogenphosphate, phosphate, nitrate, hydrofluorosilicate or fluorosilicate. $C_1$-$C_{18}$ carboxylate is for example an aliphatic or olefinic carboxylate, preferably an aliphatic $C_1$-$C_{13}$ carboxylate, very preferably an aliphatic $C_1$-$C_6$ carboxylate and especially formate, acetate or proprionate. Preferred is $C_1$-$C_{18}$ carboxylate, fluoride, chloride, sulfonate, hydrogensulfate, sulfate, dihydrogen phosphate, hydrogenphosphate, phosphate or nitrate. Very preferred is aliphatic or olefinic $C_1$-$C_{18}$ carboxylate, particularly preferred is formate, acetate or proprionate.

Preferred is a method, wherein the anion is $C_1$-$C_{18}$ carboxylate, fluoride, chloride, bromide, iodide, sulfonate, hydrogensulfate, sulfate, dihydrogenphosphate, hydrogenphosphate, phosphate, nitrate, hydrofluorosilicate or fluorosilicate.

In case $R^2$ is H and $R^3$ is —X—$NH_2$, formula I is also expressed by formula II

(II)

Preferred is a method, wherein at formula I $R^1$ is $C_9$-$C_{15}$ alkyl, which is linear or branched, $R^2$ is H, $R^3$ is —X—$NH_2$ and X is $C_2$-$C_4$ alkylene, which is linear or branched.

Preferred is a method, wherein at formula I X is —$CH_2$—$CH_2$— or —$CH_2$—$CH_2$—$CH_2$—.

Preferred is a method, wherein at formula I $R^1$ is $C_{10}$-$C_{14}$ alkyl, which is linear or branched.

Preferred is a method, wherein the compound of formula I is compound (101) or compound (102)

The compound of formula I is added preferably in an amount of 10 g to 300 g per ton of the ore. The calculation is performed on basis of dry ore. The amount is very preferably from 20 g to 200 g per ton of the ore, particularly preferably from 30 g to 150 g per ton of the ore, especially from 40 g to 120 g per ton of the ore and very especially from 50 g to 90 g per ton of the ore.

Preferred is a method, wherein the compound of formula I is added in an amount between 10 g to 300 g per ton of the ore.

The pH value at the steps (c) and (d) of the method is preferably adjusted with a pH regulator to a specific pH value, typically to a pH value between 8 and 12, particularly between 9 and 11. A pH regulator is typically a strong base, for example sodium hydroxide, potassium hydroxide, sodium carbonate or potassium carbonate. Preferably, the pH value of the aqueous pulp is between 8 and 12, particularly between 9 and 11. Preferably, step (c), i.e. adding the compound of formula to the aqueous pulp, takes place at a pH value between 8 and 12, particularly between 9 and 11. Preferably, the pH value of the aqueous mixture is between 8 and 12, particularly between 9 and 11. Preferably, step (d), i.e. aerating the aqueous mixture, takes place at a pH value between 8 and 12, particularly between 9 and 11. Preferably, (e), i.e. obtaining the concentrate enriched in iron mineral content, takes place at a pH value between 8 and 12, particularly between 9 and 11 A regulation of the pH value supports that the ore, especially the particles of the ore, exhibit the correct surface charge.

Preferred is a method, wherein the pH value at step (c) is between 8 and 12.

Preferred is a method, wherein the pH value at step (c) and at step (b) is between 8 and 12.

Preferred is a method, wherein the pH value at step (c) and at step (d) is between 8 and 12.

Preferred is a method, wherein the pH value at step (c), at step (b) and at step (d) is between 8 and 12.

Preferred is a method, wherein the pH value at step (c), at step (b), at step (d) and at step (e) is between 8 and 12.

A flotation auxiliary is for example a depressing agent, a froth regulator, a co-collector or an extender oil.

A depressing agent helps to prevent flotation of an ingredient of the ore, which is not desired to get part of the froth or supports in general the selectivity of the method of manufacturing the concentrate. A depressing agent is for example a hydrophilic polysaccharide, particularly a starch, or sodium silicate. The starch is for example a native starch or a modified starch. A native starch is for example a starch from corn, wheat, oat, barley, rice, millet, potato, pea, tapioca or manioc. The native starch is preferably pregelatinized, i.e. warmed for starch gelatination. A modified starch is either a degraded starch, which possesses a reduced weight-average molecular weight versus the original starch, a chemically modified starch or a degraded and chemically modified starch. A degradation of starch is for example possible by oxidation or treatment by acid, base or enzymes. The degradation leads typically to an increased content on oligosaccharides or dextrines. A chemical modification is a functionalization of a starch by covalent linkage of a chemical group to the starch. A chemically modified starch is for example obtainable by esterification or etherification of a starch. The esterification of an acid with a starch is for example performed with an anhydride of the acid or a chloride of the acid. The etherification of a starch is for example possible with an organic reagent, which contains a reactive epoxide functionality. Preferred is a depressing agent, which is a native starch, particularly a pregelatinized starch. A depressing agent is preferably added in an amount of 100 to 3000 g per ton of the ore. The calculation is performed on basis of dry ore. The amount is very preferably from 300 g to 2200 g per ton of the ore, particularly preferably from 400 g to 1900 g per ton of the ore, especially from 500 g to 1700 g per ton of the ore and very especially from 600 g to 1400 g per ton of the ore.

A froth regulator helps to improve the efficiency of the method of manufacturing by interfering with the froth generation. A froth property is for example the froth height respectively the volume of the froth or the stability of the froth, i.e. the time to collapse after stop of aerating. A froth regulator is for example pine oil, methylisobutyl carbinol, $C_6$-$C_{12}$ alcohol, particularly 2-ethylhexanol or hexanol, an alcoholic ester, particularly a mixture comprising 2,2,4-trimethyl-1,3-pentan-diolmonoisobutyrate, terpineol, triethoxybutane, an alkoxylated alcohol, particularly an ethoxylated and/or propoxylated alcohol, polyethylene glycol or polypropylene glycol.

A co-collector is a surface-active compound, which is different to a compound of formula I. A co-collector is for example cationic, non-ionic or anionic, preferably cationic or non-ionic and very preferably cationic. A cationic co-collector is for example $C_9$-$C_{18}$ alkylamine, 2-($C_9$-$C_{18}$ alkylamino)ethyl-1-amine, N'—($C_9$-$C_{18}$ alkyl)propane-1,3-diamine, 3-($C_9$-$C_{18}$ alkoxy)propyl-1-amine, N'-(3-($C_9$-$C_{18}$ alkoxy)propyl)propane-1,3-diamine. A non-ionic co-collector is for example $C_9$-$C_{15}$ alkyl alcohol, which is branched, or ethoxylated $C_9$-$C_{15}$ alkyl alcohol, which is branched and ethoxylated with 2 to 4 mole ethylene oxide. In case of a co-collector as a flotation auxiliary, the co-collector might be added together with the compound of formula I. In this case, this part of step (b) occurs simultaneously with step (c).

An extender oil is for example kerosene.

Preferred is a method, wherein at step (b) one or more flotation auxiliaries are added and one of the flotation auxiliaries is a depressing agent, a froth regulator, a co-collector or an extender oil.

Preferred is a method, wherein one of the flotation auxiliaries added at step (b) is a depressing agent.

Preferred is a method, wherein one of the flotation auxiliaries added at step (b) is a depressing agent, which is a starch.

Preferred is a method, wherein one of the flotation auxiliaries added at step (b) is a depressing agent and one of the flotation auxiliaries is a co-collector, which is added at step (b) before step (c) or is added simultaneously with the compound of formula I.

In the method of manufacturing a concentrate, conventional inverse flotation plant equipment may be used. Preferably, the compound of formula I and optionally a flotation auxiliary, which is a co-collector, is or are added to the aqueous pulp, which is already in the flotation cell, which is used for aerating the mixture in step (d).

After adding of a compound of formula I to the aqueous pulp, the obtained aqueous mixture is preferably kept, particularly under stirring, for a conditioning period before aerating the aqueous mixture. This allows the compound of formula I and optionally a flotation auxiliary, which is a co-collector, to condition the ore, particularly the ore particles, in the aqueous mixture. The conditioning period lasts for example for one minute or up to 10 or 15 minutes.

At aerating the aqueous mixture, air is typically injected into the base of the flotation cell. Air bubbles are formed and rise to the surface and generate the froth at the surface. The injection of air may be continued until no more froth is formed. This might last for example for one minute or up to 15 or 20 minutes. The froth is removed.

For obtaining the concentrate enriched in iron mineral content, aerating is typically stopped. The concentrate enriched in iron mineral content sinks typically to the bottom of the flotation cell.

In some cases, it may be desirable to treat the concentrate enriched in iron mineral content in a similar manner again. For example, the steps (c) and (d) are repeated as step (d-c) followed by step (d-d) before step (e) is conducted.

The concentrate enriched in iron mineral content contains preferably at least 60% by weight of Fe atoms based on the overall weight of the concentrate enriched in iron mineral content, very preferably at least 65% by weight. The weight of Fe atoms is similar to the weight of iron content. The concentrate enriched in iron mineral content contains preferably less than 2% by weight of $SiO_2$ based on the overall weight of the concentrate enriched in iron mineral, very preferably less than 1.9% by weight and particularly preferably 1.8% or less than 1.8% by weight of $SiO_2$. The concentrate enriched in iron mineral content contains preferably at least 60% by weight of Fe atoms and less than 2% by weight of $SiO_2$ based on the overall weight of the concentrate enriched in iron mineral content, very preferably at least 65% by weight of Fe atoms and less than 1.9% by weight of $SiO_2$.

The above described preferences for the method of manufacturing a concentrate or for the added compound of formula I are described for the method. These preferences apply also to the further embodiments of the invention.

A further embodiment of the invention is a use of a compound of formula I wherein $R^1$ is $C_9$-$C_{22}$ alkyl or alkenyl, which is linear or branched, $R^2$ is H, $C_1$-$C_4$ alkyl, which is linear or branched, $R^3$ is —X—$NH_2$, H or $C_1$-$C_4$ alkyl, which is linear or branched, and X is $C_2$-$C_4$ alkylene, which is linear or branched, or a salt of a protonated compound of formula I and an anion as a flotation collector for manufacturing a concentrate enriched in iron mineral content from an ore, which contains an iron mineral and silicate, by a reverse flotation.

Preferred is a use of an amine as a flotation collector for manufacturing a concentrate enriched in iron mineral content from an ore, which contains an iron mineral and silicate, by a reverse flotation, characterized in that the amine is a compound of formula I wherein $R^1$ is $C_9$-$C_{22}$ alkyl or alkenyl, which is linear or branched, $R^2$ is H, $C_1$-$C_4$ alkyl, which is linear or branched, $R^3$ is —X—$NH_2$, H or $C_1$-$C_4$ alkyl, which is linear or branched, and X is $C_2$-$C_4$ alkylene, which is linear or branched, or a salt of a protonated compound of formula I and an anion.

Preferred is a use, wherein at formula I $R^1$ is $C_9$-$C_{15}$ alkyl, which is linear or branched, $R^2$ is H, $R^3$ is —X—$NH_2$ and X is $C_2$-$C_4$ alkylene, which is linear or branched.

A further embodiment of the invention is a compound of formula I wherein at formula I $R^1$ is $C_9$-$C_{15}$ alkyl, which is linear or branched, $R^2$ is H, $R^3$ is —X—$NH_2$ and X is $C_2$-$C_4$ alkylene, which is linear or branched, or a salt of a protonated compound of formula I and an anion.

A further embodiment of the invention is a method for manufacturing a compound of formula I wherein at formula I $R^1$ is $C_9$-$C_{15}$ alkyl, which is linear or branched, $R^2$ is H, $R^3$ is —X—$NH_2$ and X is $C_2$-$C_4$ alkylene, which is linear or branched, which method comprises the step of

(I) reacting a compound of formula INT-I-1 and a base,
or a compound of formula INT-I-2 with a compound of the formula INT-II to obtain the compound of formula I.

It has been found that the reaction of a compound of formula INT-II with a compound of formula INT-I-1 and a base or a compound of formula INT-I-2 results in a compound of formula I in a chemically relatively pure form. Normally, one might expect that the generated molecules of a compound of formula I would react further with a compound of formulae INT-I-1 or INT-I-2 in view of one primary and two secondary amine functionalities in the compound of formula I. One might also expect that the compound of formulae INT-I-1 or INT-I-2 reacts with itself in view of the secondary amine functionality. Chemically relatively pure means in this context that of the isolated material, at least 75% of the molar amount of a compound of formulae INT-I-1 and INT-I-2 reacts to a compound of formula I, preferably 80% to 100%, very preferably 85% to 100% and particularly preferably 90% to 100%.

The base is for example a sodium alkoxylate, a potassium alkoxylate, sodium hydroxide or potassium hydroxide. The alkoxylate is for example methoxylate, ethoxylate or propoxylate.

The reacting takes preferably place in a solvent or free of a solvent, very preferably in a solvent, which is an alcohol, an ether or a keton, particularly preferably in a solvent, which is an alcohol, and especially preferably in a solvent, which is methanol, ethanol, propanol or butanol.

The molar ratio between the sum of the compound of formula INT-I-1 and the compound INT-I-2 and the compound of formula INT-II is preferably from 0.1 to 1.2, very preferably from 0.15 to 1.1, particularly preferably between 0.18 to 1 and especially preferably between 0.2 to 0.9.

FIGS. 1 to 8 are attached and described below.

FIG. 2 shows a $^1$H-NMR spectrum between around 0.5 ppm and around 4.0 ppm of the material obtained at A-2 in $CDCl_3$. FIG. 2 is an enlarged extract from FIG. 1.

FIG. 7 shows a $^1$H-NMR spectrum between around 2.30 ppm and around 2.95 ppm of the material obtained at A-4 in $CDCl_3$. FIG. 7 is an enlarged extract from FIG. 6.

The following examples illustrate further the invention without limiting it. Percentage values are percentage by weight if not stated differently.

A) Employed Collectors and Precursor

A-1: N'-(isotridecoxypropyl)propane-1,3-diamine

Isotridecanol N (degree of branching ~2.2) is reacted in a Michael addition with acrylonitrile in a molar ratio of 1:1. This is followed by hydrogenating the intermediate over Raney cobalt to generate 3-isotridecoxypropan-1-amine. In a following stage, additional acrylonitrile is added in a molar ratio of 1:1 and reacted in a Michael addition. Afterwards, a hydrogenation over Raney cobalt is conducted. The obtained material contains as measured by gas chromatography 2.9% isotridecanol N, 11.7% isotridecoxypropane-1-amine, 78.1% N'-(isotridecoxypropyl)propane-1,3-diamine (as depicted as compound (301)) and 4.0% N'-[3-(3-tridecoxypropylamino)propyl]propane-1,3-diamine. The obtained material is used in as comparative material A-1. The obtained material is a common type of amine collector for iron ore benefication as described in WO 2012-139985 and acts by removing silica in an inverse flotation process.

A-2: 1-Chloro-3-(dodecylamino)propan-2-ol

A stirred solution of dodecylamine (200 g, 1.08 mol) in isopropanol (540 mL) is cooled to 15° C. and epichlorohydrin (100 g, 1.08 mol) is added dropwise. The addition rate is adjusted so that the reaction mixture does not exceed 30° C. After complete addition, the reaction mixture is stirred for 18 h at ambient temperature and then cooled in an ice bath. The white precipitate is collected by filtration, washed with cold isopropanol and dried under vacuum. 1-Chloro-3-(dodecylamino)propan-2-ol (116 g, 38%/depicted as compound (201)/CAS-No. 1191-55-5) is obtained as a white solid.

Figure 1:
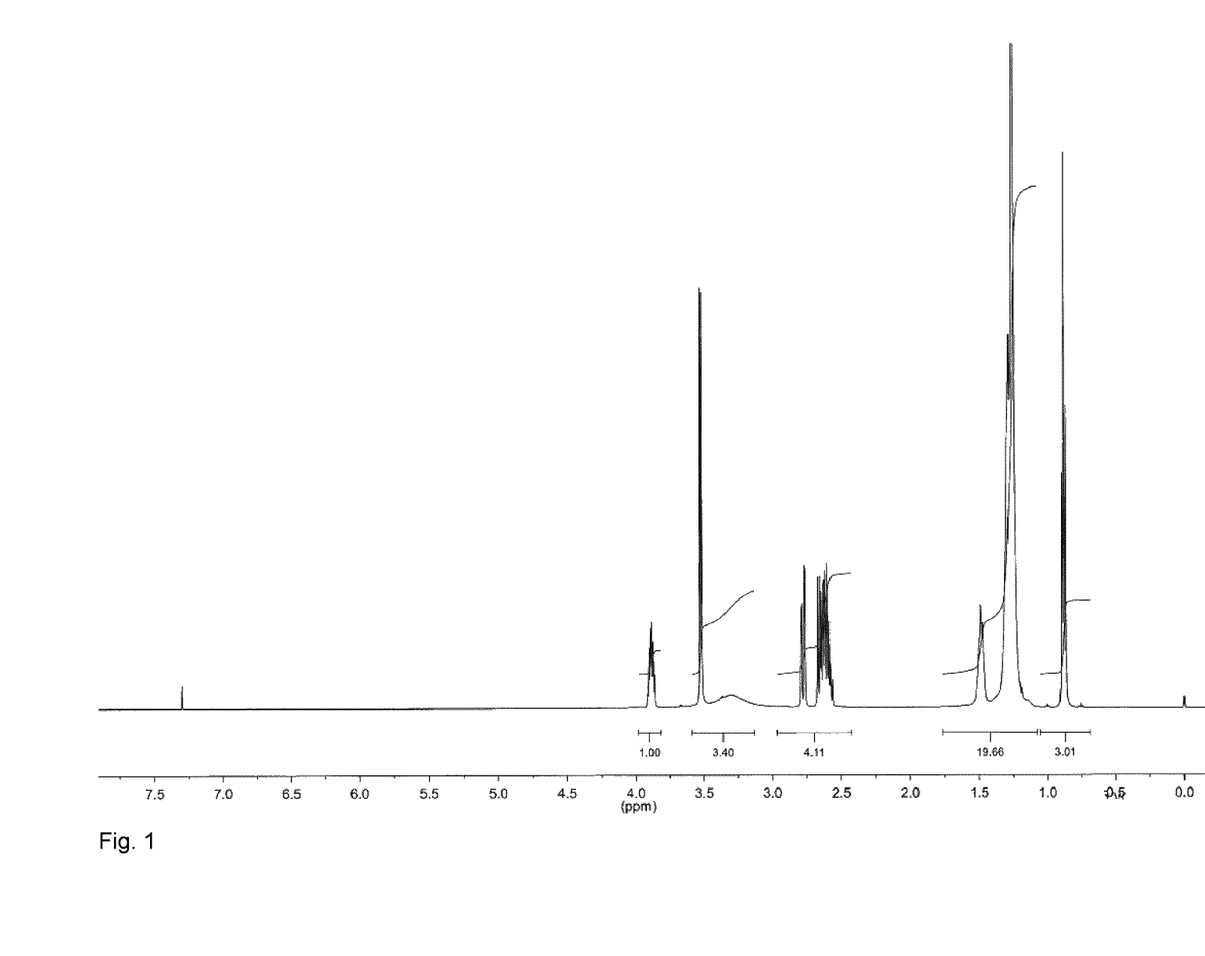
FIG. 1 shows a $^1$H-NMR spectrum in $CDCl_3$ of the material obtained at A-2.
Figure 2:
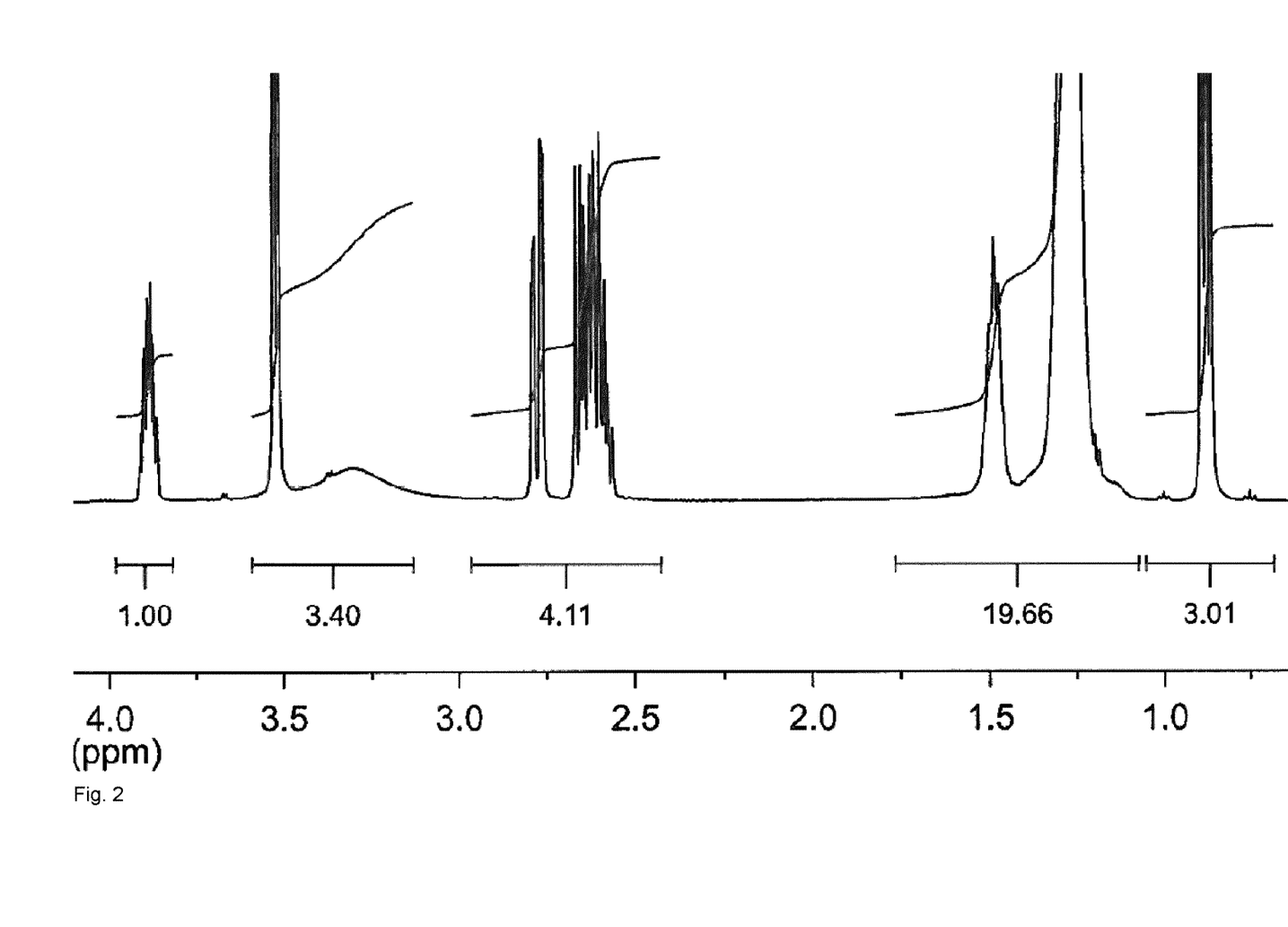
Figure 3:
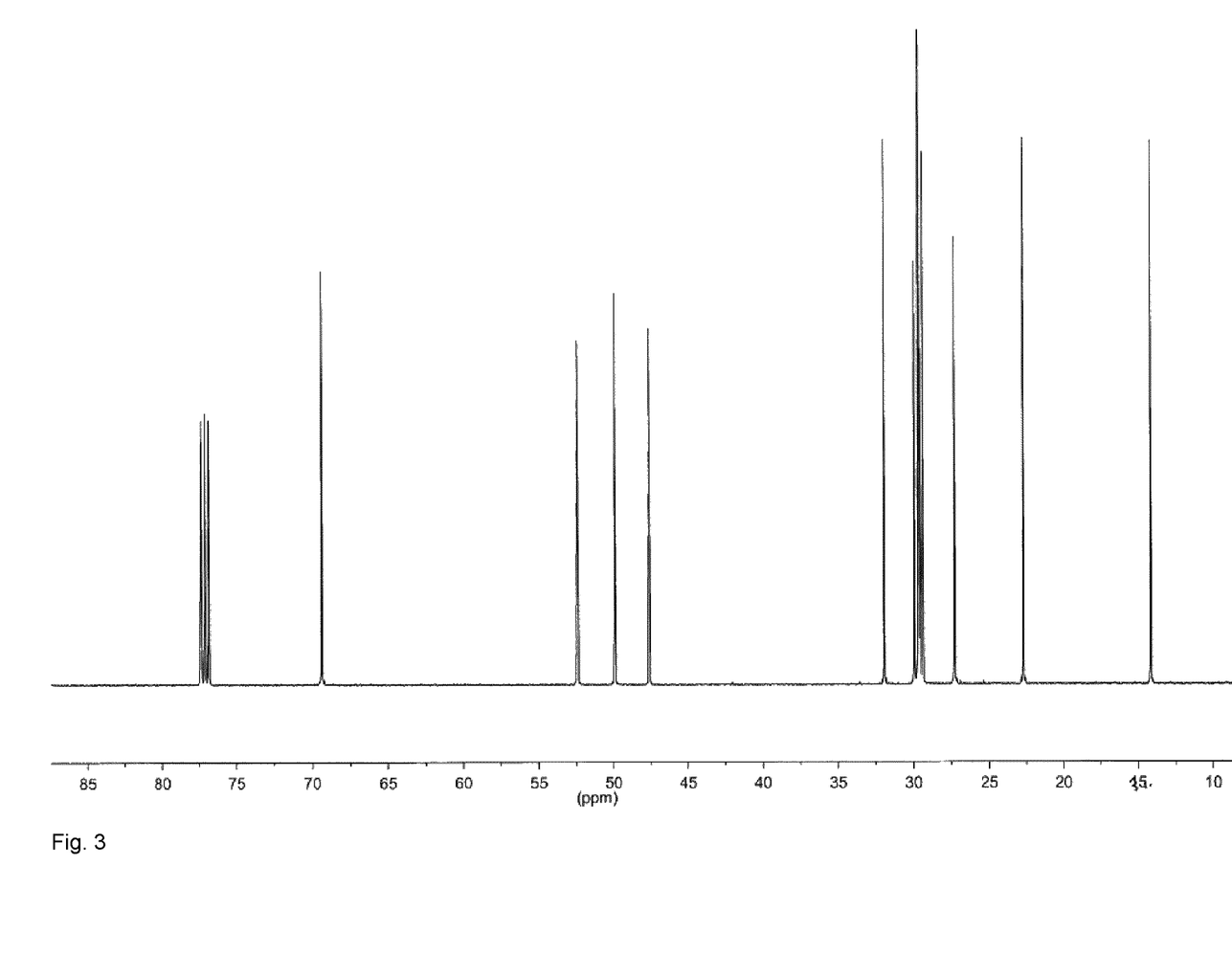
FIG. 3 shows a $^{13}$C-NMR spectrum in $CDCl_3$ of the material obtained at A-2.

$^1$H-NMR (500 MHz) and $^{13}$C-NMR (125 MHz) spectra of the white solid are measured in CDCl$_3$. FIG. 1 and FIG. 2 depict the $^1$H-NMR spectra. FIG. 3 depicts the $^{13}$C-NMR spectrum.

A-3: 1-((2-aminoethyl)amino)-3-(dodecylamino)propan-2-ol

Material obtained from A-2 (100 g, 0.36 mol calculated based on 1-chloro-3-(dodecylamino)propan-2-ol) and ethane-1,2-diamine (108 g, 1.80 mol) are dissolved in ethanol (800 mL). A solution of sodium methylate in methanol (25.3 weight-%, 81.3 g, 0.38 mol) is added dropwise at ambient temperature and the mixture is stirred overnight. The obtained suspension is filtered and the filter cake is washed with ethanol. The combined filtrates are concentrated under reduced pressure and the residue is dried under vaccuum (95° C., 15 mbar) to obtain a material consisting mainly of 1-((2-aminoethyl)amino)-3-(dodecylamino)propan-2-ol (97.8 g, 90% calculated based on 1-((2-aminoethyl)amino)-3-(dodecylamino)propan-2-ol/depicted as compound (101)) as a white solid.

Figure 4:
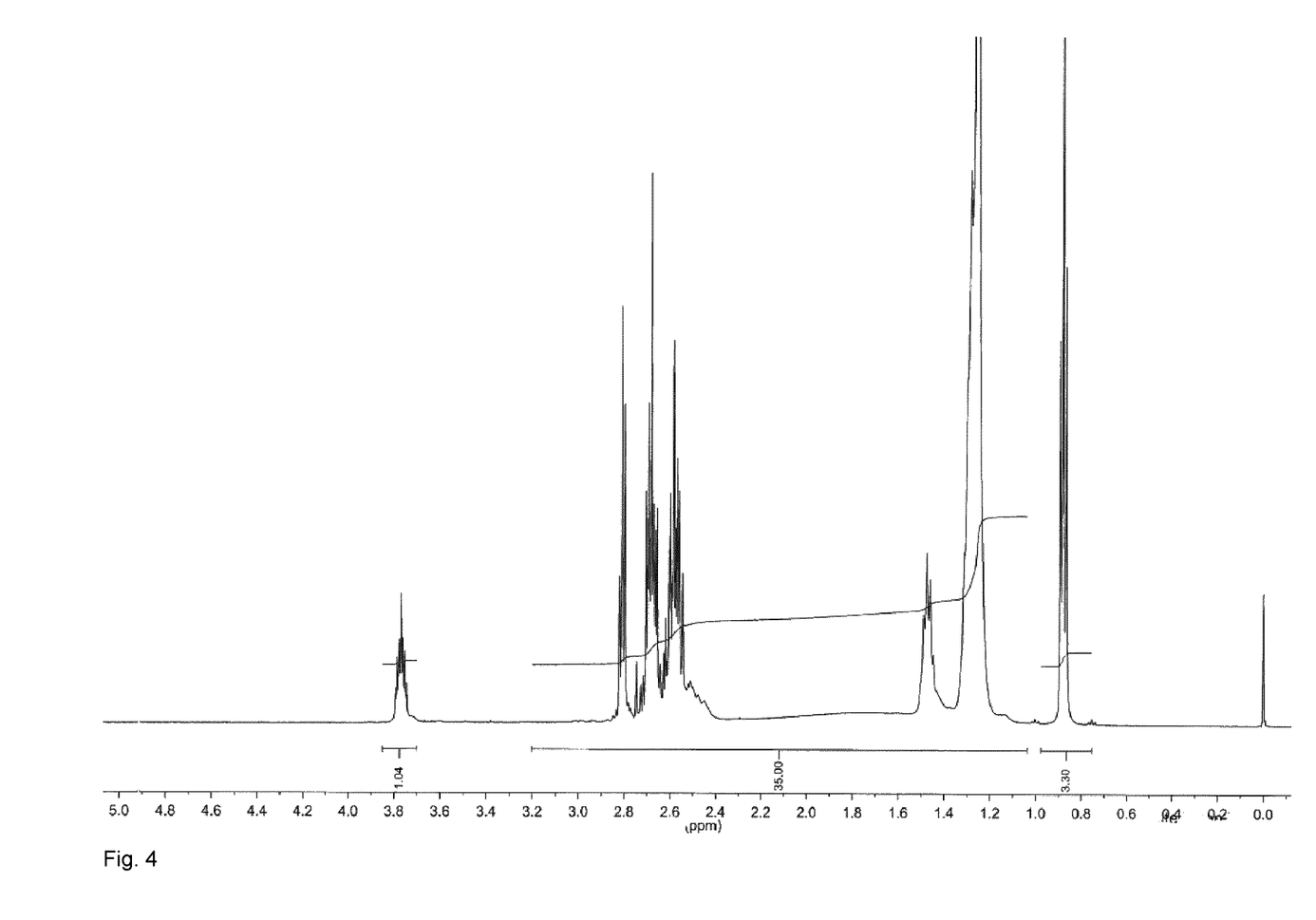
FIG. 4 shows a $^1$H-NMR spectrum in $CDCl_3$ of the material obtained at A-3.
Figure 5:
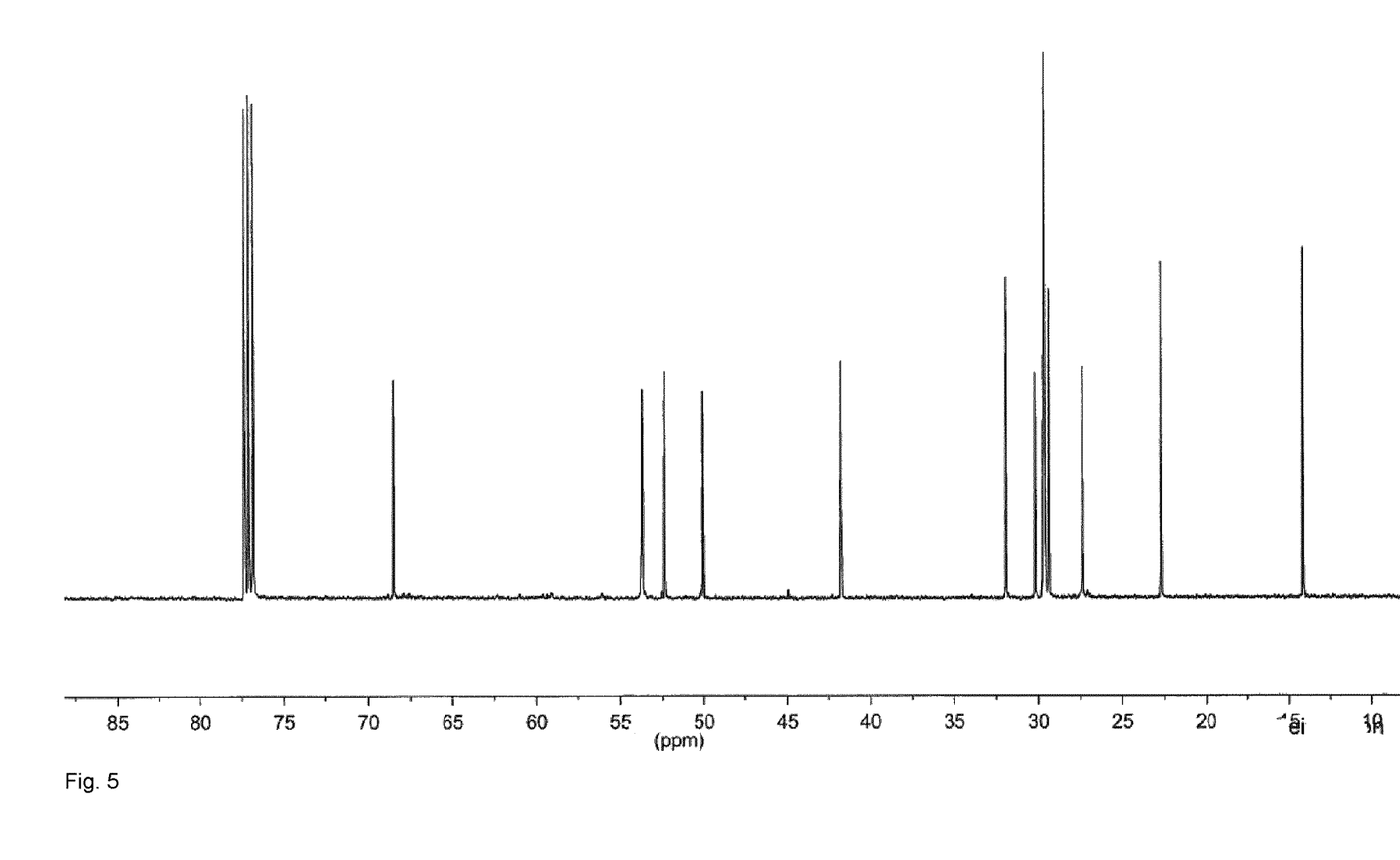
FIG. 5 shows a $^{13}$C-NMR spectrum in $CDCl_3$ of the material obtained at A-3.

$^1$H-NMR (500 MHz) and $^{13}$C-NMR spectra (125 MHz) of the white solid are measured in CDCl$_3$. FIG. 4 depicts the $^1$H-NMR spectra. FIG. 5 depicts the $^{13}$C-NMR spectrum.

A-4: 1-((3-aminopropyl)amino)-3-(dodecylamino)propan-2-ol

Material obtained from A-2 (100 g, 0.36 mol calculated based on 1-chloro-3-(dodecylamino)propan-2-ol) and propane-1,3-diamine (133 g, 1.79 mol) are dissolved in ethanol (800 mL). A solution of sodium methylate in methanol (25.3 weight-%, 81.3 g, 0.38 mol) is added dropwise at ambient temperature and the mixture is stirred overnight. The obtained suspension is filtered and the filter cake is washed with ethanol. The combined filtrates are concentrated under reduced pressure and the residue is dried under vaccuum (95° C., 15 mbar) to obtain a product consisting mainly of 1-((3-aminopropyl)amino)-3-(dodecylamino)propan-2-ol (102 g, 90% calculated based on 1-((3-aminopropyl)amino)-3-(dodecylamino)propan-2-ol/depicted as compound (102)) as a white solid.

Figure 6:
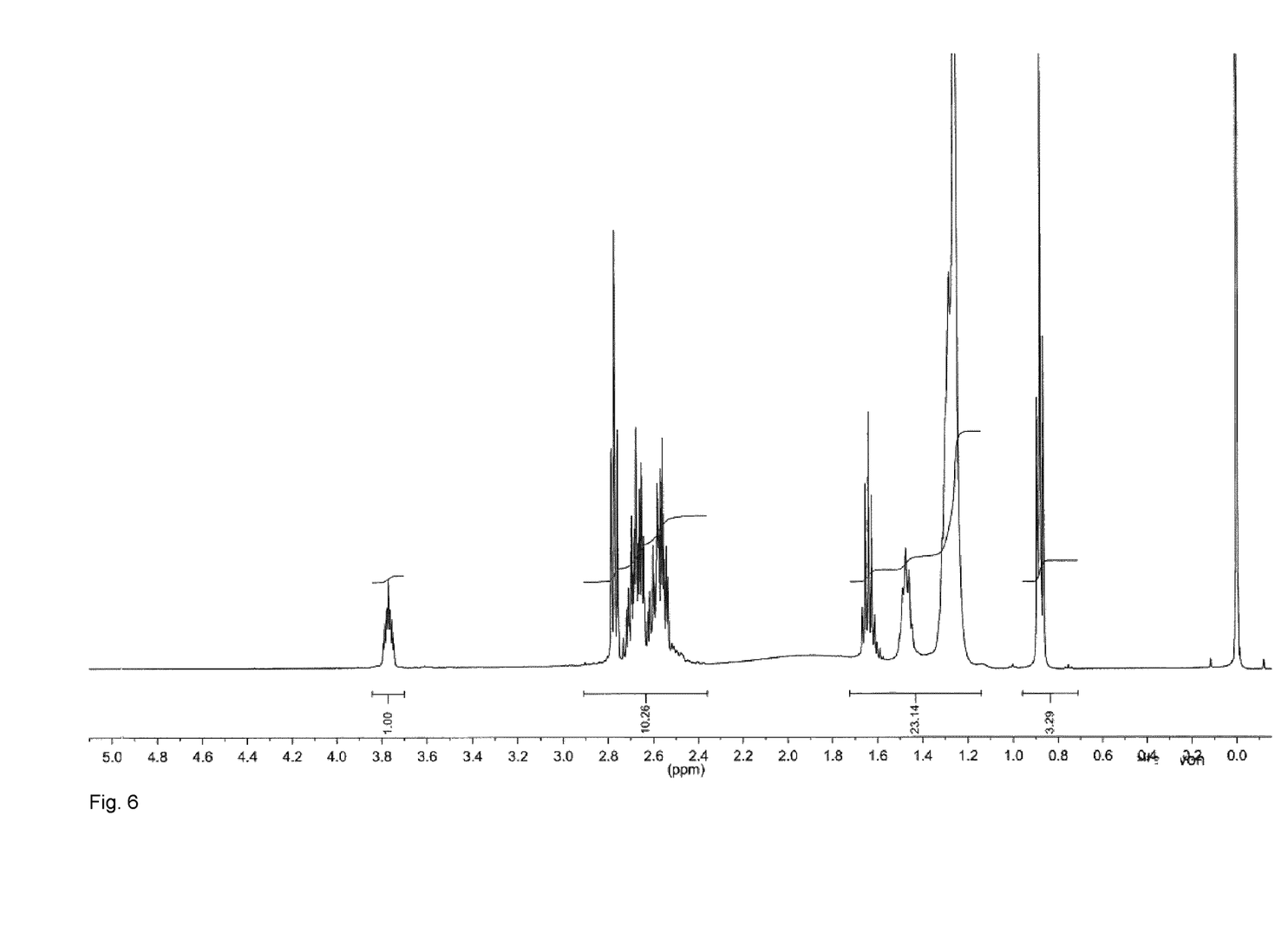
FIG. 6 shows a $^1$H-NMR spectrum in $CDCl_3$ of the material obtained at A-4.
Figure 7:
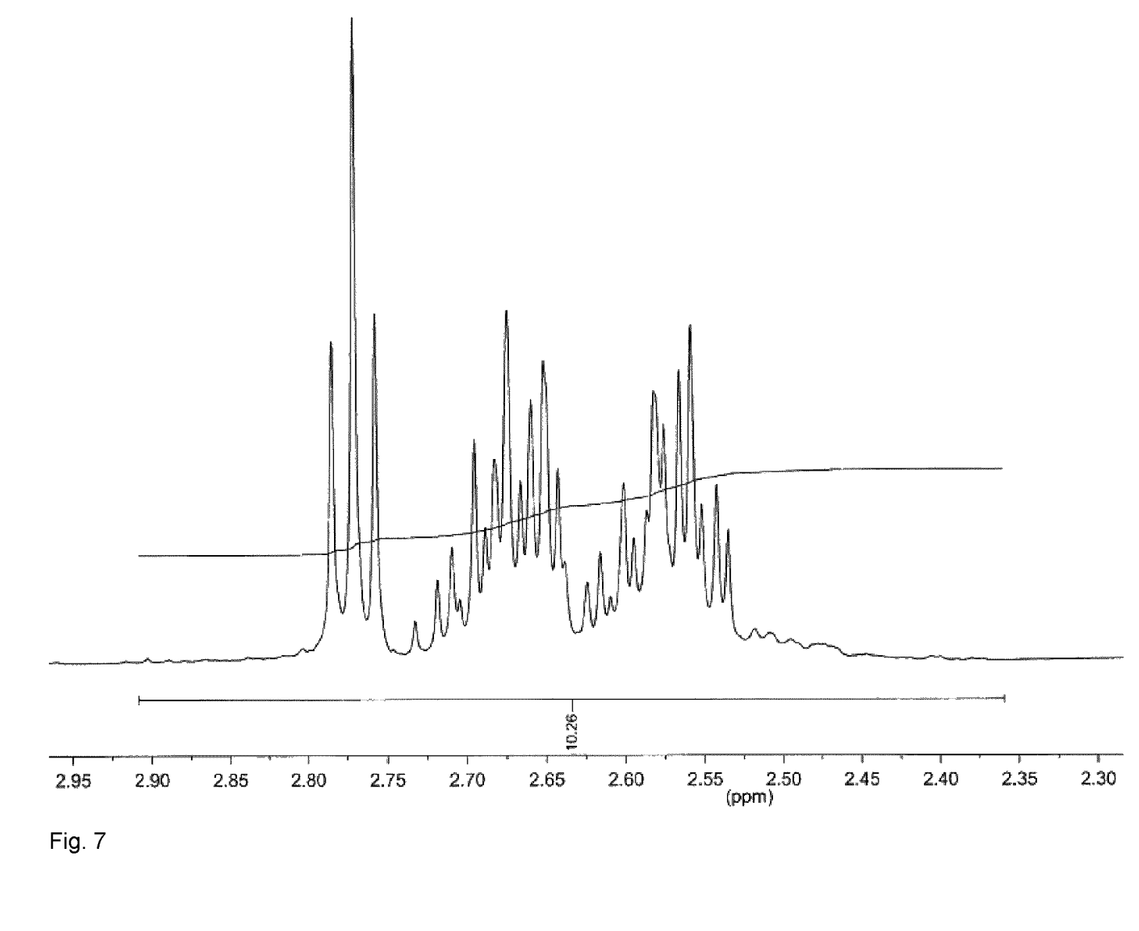
Figure 8:
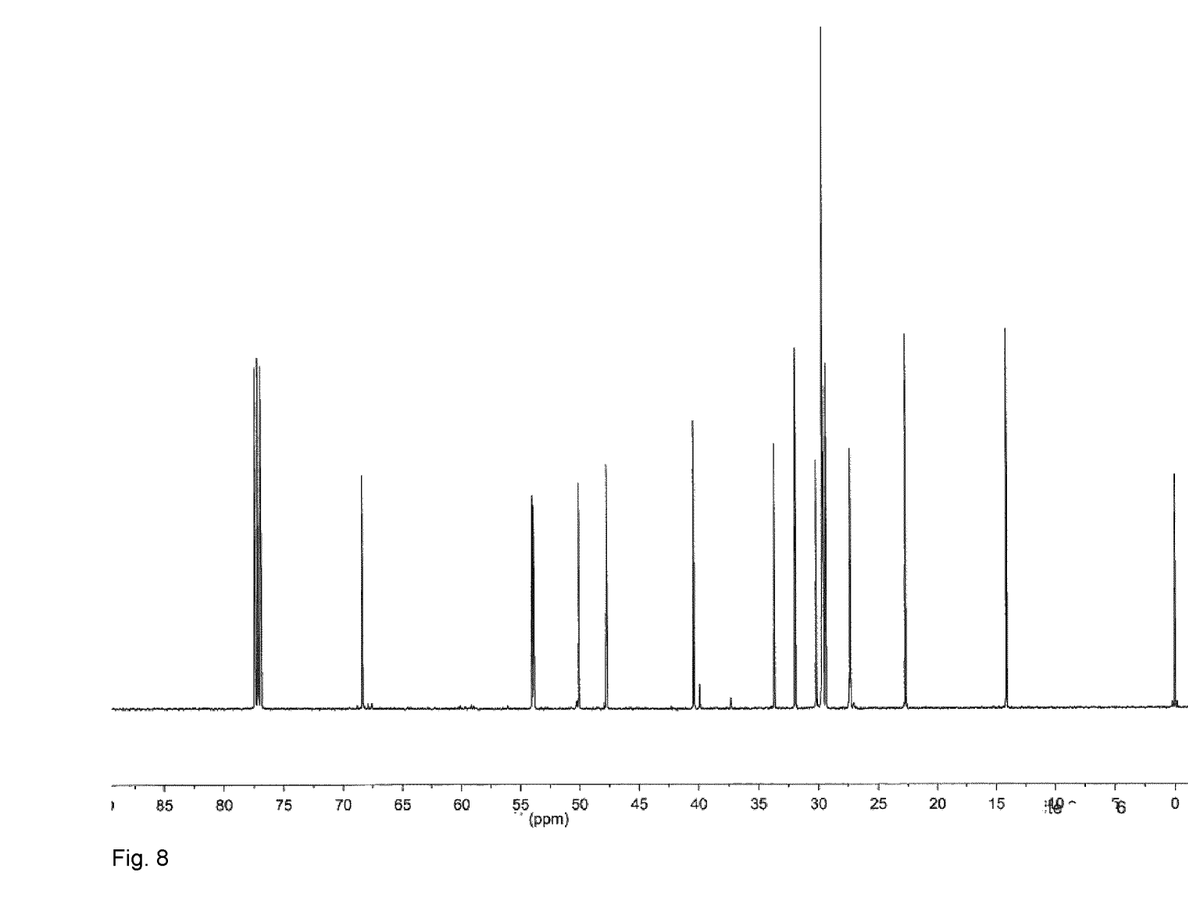
FIG. 8 shows a $^{13}$C-NMR spectrum in $CDCl_3$ of the material obtained at A-4.

$^1$H-NMR (500 MHz) and $^{13}$C-NMR (125 MHz) spectra of the white solid are measured in CDCl$_3$. FIG. 6 and FIG. 7 depict the $^1$H-NMR spectra. FIG. 8 depicts the $^{13}$C-NMR spectrum.

B) Flotation

The following examples illustrate further the invention without limiting it. Percentage values are percentage by weight if not stated differently.

500 g of ore (hematite based, 63% Fe$_2$O$_3$[44% Fe atom], 34% SiO$_2$), which is ground to such a particle size that 80% passes 100 m (measured by standard dry sieving), is placed in a 1.5 flotation cell of a Denver D10 flotation machine. 500 mL of distilled water is added at ambient temperature (~21° C.), which results in the formation of a 50% solids. This pulp is conditioned with pregelatinized corn starch in an amount of 1000 g/t (calculated based on ton of dry ore) calculated as dry starch for 3 minutes at 1000 rpm. Afterwards, the pH is adjusted to 9.5 with aqueous 5% sodium hydroxide solution. A collector as stated in table B-1 in an amount of 70 g/t (calculated based on ton of dry ore) is added in form of a 1% aqueous solution, which is prepared with distilled water. The pH is adjusted to 10.5 with aqueous 5% sodium hydroxide solution and the pulp is further conditioned for 1 minute under the same rotation. After conditioning, the vessel volume is filled with distilled water until 2 cm below the lip level under a rotation of 1000 rpm. The pH is again adjusted to 10.5 with aqueous 5% sodium hydroxide solution. Afterwards, the aeration is opened and the froth is collected in a 2 L tray until complete exhaustion. The collected and solids-bearing froth in the tray and the remaining cell fraction are separately dewatered, dried and weighed. Fe— and $SiO_2$-content of both are analyzed by EDXRF measurement on a lithium borate based fused bead. The results are listed in table B-1.

TABLE B-1

| example | collector | Fe conc. grade [c] [Fe atom weight in percent] | $SiO_2$ conc. grade [d] [$SiO_2$ weight in percent] | Fe recovery [e] [Fe atom weight in percent] | $SiO_2$ loss [f] [%] |
|---|---|---|---|---|---|
| B-1 [a] | A-1 | 70 | 1.2 | 91.5 | 97.9 |
| B-2 [b] | A-3 | 70 | 1.4 | 93.5 | 96.6 |
| B-3 [b] | A-4 | 69 | 1.8 | 93.8 | 97.9 |

Food notes:
[a] comparative
[b] according to invention
[c] Fe conc. grade means Fe atom content in cell fraction
[d] $SiO_2$ conc. grade means $SiO_2$ content in cell fraction
[e] recovery is the ratio between the overall amount of Fe atom contained in the cell fraction and the overall amount of Fe atom contained in the ore employed as starting material
[f] $SiO_2$ loss is the amount of $SiO_2$ removed from the cell fraction and expressed in percentage based on the amount of $SiO_2$ contained in the ore employed as starting material The results in table B-1 shows that a targeted concentrate grade of <2.0% $SiO_2$ and >67% Fe is met for B-1, B-2 and B-3. At this desired grade, the examples B-2 and B-3 provide a higher recovery of valuable iron ore concentrate.

The invention claimed is:

1. A method for manufacturing a concentrate enriched in iron mineral content from an ore, which contains an iron mineral and silicate, by a reverse flotation, method comprising:
adding a compound of formula I wherein $R^1$ is $C_9$-$C_{22}$ alkyl or alkenyl, which is linear or branched, $R^2$ is H or $C_1$-$C_4$ alkyl, which is linear or branched, $R^3$ is -X-$NH_2$, H or $C_1$-$C_4$ alkyl, which is linear or branched, and X is $C_2$-$C_4$ alkylene, which is linear or branched, or a salt of a protonated compound of formula I and an anion, to a prepared aqueous pulp of the ore and optionally one or more flotation auxiliaries to obtain an aqueous mixture.

2. The method according to claim 1, comprising:
providing the ore, which contains the iron mineral and silicate,
preparing the prepared aqueous pulp from the provided ore by addition of water, and optionally one or more flotation auxiliaries,
adding the compound of formula I
to the prepared aqueous pulp of the ore, and optionally one or more flotation auxiliaries, to obtain the aqueous mixture,
aerating the aqueous mixture in a flotation cell to generate a froth, which is enriched in silicate content, and removing the generated froth from the flotation cell, and
obtaining from the flotation cell the concentrate enriched in iron mineral content.

3. The method according to claim 1, wherein $R^1$ is $C_9$-$C_{15}$ alkyl, which is linear or branched, $R^2$ is H, $R^3$ is -X-$NH_2$ and X is $C_2$-$C_4$ alkylene, which is linear or branched.

4. The method according to claim 1, wherein X is -$CH_2$-$CH_2$- or -$CH_2$-$CH_2$-$CH_2$-.

5. The method according to claim 1, wherein $R^1$ is $C_{10}$-$C_{14}$ alkyl, which is linear or branched.

6. The method according to claim 1, wherein the compound of formula I is compound (101) or compound (102)

(101)

(102)

7. The method according to claim 1, wherein the anion is $C_1$-$C_{18}$ carboxylate, fluoride, chloride, bromide, iodide, sulfonate, hydrogensulfate, sulfate, dihydrogenphosphate, hydrogenphosphate, phosphate, nitrate, hydrofluorosilicate or fluorosilicate.

8. The method according to claim 1, wherein the compound of formula I is added in an amount between 10 g to 300 g per ton of the ore.

9. The method according to claim 1, wherein the adding of the compound of formula I is at a pH value between 8 and 12, where the pH is to the prepared aqueous pulp during the adding of the compound of formula I.

10. The method according to claim 2, wherein the one or more flotation auxiliaries are required and comprises a depressing agent, a froth regulator, a co-collector or an extender oil.

11. The method according to claim 10, wherein the depressing agent comprises a starch.

* * * * *